US012575907B2

(12) United States Patent
Welfers et al.

(10) Patent No.: US 12,575,907 B2
(45) Date of Patent: Mar. 17, 2026

(54) PROTECTIVE DEVICE FOR THE HAND OF A MEDICAL PERSONNEL WHEN PUNCTURING AN UMBILICAL CORD OF NEONATES

(71) Applicant: pfm medical GMBH, Cologne (DE)

(72) Inventors: Pia Welfers, Wegberg (DE); Bianca Haase, Tübingen (DE); Georg Kox, Wegberg (DE); Daniel Rauch, Essen (DE)

(73) Assignee: PFM Medical GmbH (DE)

( * ) Notice: Subject to any disclaimer, the term of this patent is extended or adjusted under 35 U.S.C. 154(b) by 352 days.

(21) Appl. No.: 18/169,530

(22) Filed: Feb. 15, 2023

(65) Prior Publication Data

US 2023/0255717 A1 Aug. 17, 2023

(30) Foreign Application Priority Data

Feb. 16, 2022 (IT) ......................... 102022000002870

(51) Int. Cl.
*A61B 90/00* (2016.01)
*A61B 5/15* (2006.01)

(52) U.S. Cl.
CPC ...... *A61B 90/08* (2016.02); *A61B 2090/0801* (2016.02)

(58) Field of Classification Search
CPC ........ A61B 5/150038; A61B 5/150259; A61B 5/15; A61B 90/08; A61B 2090/0801;
(Continued)

(56) References Cited

U.S. PATENT DOCUMENTS 3,976,080 A * 8/1976 Bornhorst ......... A61M 16/0488
604/179
9,375,168 B2 * 6/2016 Shacham ......... A61B 5/150366
(Continued)

FOREIGN PATENT DOCUMENTS

CN 2647262 Y 10/2004
DE 102009047666 * 6/2011
(Continued)

OTHER PUBLICATIONS

Search Report for Chinese Patent Application No. 2023100923190 dated Jun. 23, 2025, 2 pages.
(Continued)

*Primary Examiner* — Tan-Uyen T Ho
*Assistant Examiner* — Lindsey R. Rivers
(74) *Attorney, Agent, or Firm* — Lisa E. Geary; Eckert Seamans Cherin & Mellott LLC

(57) ABSTRACT

Disclosed is a protective device for the hand of a medical personnel when puncturing an umbilical cord of neonates, comprising: an umbilical cord channel for receiving the umbilical cord of the neonate, two wings arranged at the upper edge of the umbilical channel as hand protection, the wings each extending laterally away from the umbilical channel, and two handle strips, the handle strips being arranged on the two wings and one handle strip in each case extending from the lateral wings in the depth direction of the umbilical cord channel, the height of the respective handle strips corresponding at least to the depth of the umbilical cord channel, so that the umbilical cord channel is arranged between the two handle strips.

11 Claims, 4 Drawing Sheets

(58) Field of Classification Search
    CPC ................. A61B 17/122; A61B 17/42; A61M
                       2210/1466; B26B 29/00; B26B 29/06
    See application file for complete search history.

(56)                    References Cited

U.S. PATENT DOCUMENTS

| | | | |
|---|---|---|---|
| 2002/0099258 A1* | 7/2002 | Staskin | ............ A61B 17/06109 606/1 |
| 2017/0209654 A1* | 7/2017 | Sebban | ............... A61M 5/3287 |

FOREIGN PATENT DOCUMENTS

| | | | |
|---|---|---|---|
| DE | 102009047666 A1 | 6/2011 | |
| FR | 2954085 A1 | 6/2011 | |
| WO | 2011093781 | 8/2011 | |
| WO | WO-2011093781 A1 * | 8/2011 | ........... A61B 5/1405 |

OTHER PUBLICATIONS

Office Action mailed Jan. 27, 2026 for corresponding Chinese Application No. 2023100923190.

* cited by examiner

PROTECTIVE DEVICE FOR THE HAND OF A MEDICAL PERSONNEL WHEN PUNCTURING AN UMBILICAL CORD OF NEONATES

RELATED APPLICATIONS AND CLAIM OF PRIORITY

This patent document claims priority to Italy patent application number IT 102022000002870, filed Feb. 16, 2022.

BACKGROUND

The patent document relates to a protective device for the hand of a medical personnel when puncturing an umbilical cord of neonates.

According to current regulations and guidelines, it is necessary and customary, especially for forensic reasons, to determine the pH value from the umbilical cord blood postpartum in order to obtain information about the peripartum care of the neonate. The later the cord blood is collected, the less accurate the value. Therefore, the umbilical cord is currently cut immediately after birth. This problem can be circumvented by sampling the cord blood for pH determination at the pulsatile umbilical cord. Studies have shown that the blood gas values after pulsation of the umbilical cord, due to the circulatory conversion and the increasingly persistent blood flow in the umbilical cord vessels, result in an acidotic value that does not correspond to the real situation of the child, which suggests an acidosis (hyperacidity).

It is known from studies that neonates have higher iron stores after delayed cutting of the umbilical cord, which are usually sufficient until the first year of life. In addition, neonates receive more stem cells due to the delayed cutting of the umbilical cord, which in turn has a positive effect on the neonate's immune system, hematopoiesis and central nervous system (CNS) development. Higher hemoglobin levels, better neurological and fine motor development could be observed.

Due to the birthing environment and timing restrictions, blood collection during delayed cutting of the umbilical cord presents a significant challenge to medical personnel. The mother and/or infant may move, and the umbilical cord and environment are slippery and difficult to handle due to a variety of fluids, such as amniotic fluid or blood. Therefore, there is a risk that a) the medical staff could injure themselves when taking samples with the syringe, or b) the mother and child could be injured. Such injuries also mean an increased risk of infection. In this regard, reference is also made to EU Directive 2010/32/EU on the prevention of stab and cut injuries in the healthcare sector and the Technical Rules for Biological Agents (TRBA) 250.

In order to make the collection of blood samples from the umbilical cord safer for medical personnel, various devices are known from the prior art. For example, WO 01/76660 A2 discloses a protective device for holding the umbilical cord during cord puncture. The device is channel-shaped and protects in particular against injury in the event of accidental piercing of the umbilical cord. The umbilical cord is placed in the channel-shaped protective device and fixed by the medical personnel with a finger, in particular a thumb. However, puncture injuries caused by unexpected movements of the mother and/or child are not reliably prevented, especially since the finger is positioned in the immediate vicinity of the puncture site for fixation.

FR 2 609 635 also discloses a channel-shaped protective device, but here the umbilical cord is fixed to the protective device at the distal end and proximal end by means of clamps. The umbilical cord therefore does not have to be additionally fixed with a finger during puncture. However, the umbilical cord must first be fixed by means of the clamps before it can be punctured. Furthermore, the clamps at least partially obstruct the blood flow through the umbilical cord, which can lead to falsified blood results. Comparable protective devices are known from U.S. Pat. Nos. 5,690,646 A and 5,575,795 A.

FR 2 954 085 discloses a device for sampling placental blood after the umbilical cord has been separated from the neonate. According to FR 2 954 085, sampling immediately after birth is not provided. Further, the disclosed device includes clamps for clamping the umbilical cord, which may lead to falsified blood results.

WO 2014/143664 A1 discloses a clamp which is clamped onto the umbilical cord. The clamp includes a guide for the puncture needle. A disadvantage of this device is that the puncture needle must be inserted into the guide. Furthermore, the clamp covers the puncture site and it is difficult for medical personnel to check whether the puncture needle has already been inserted into the blood vessel of the umbilical cord or whether this has also been punctured.

Furthermore, EP 2 913 004 A1 discloses a channel-shaped protective device having a fixing section and a puncture section. In the fixing section, a grip part is arranged on the underside of the channel-shaped protective device in order to fix the device between two fingers of one hand. Another finger, preferably the thumb, is used to fix the umbilical cord to the upper surface of the channel-shaped protective device. Adjacent to the fixing section is the puncture section. A finger of the medical staff is thus in close proximity to the puncture site. Also, puncture injuries caused by movements of the mother and/or neonate are not safely avoided.

SUMMARY

This document describes various embodiments of a device to protect the medical personnel as well as mother and child from puncture injuries when puncturing the umbilical cord of a neonate still connected to the mother via the umbilical cord, in particular case of unpredictable movements of mother and/or child, without affecting the blood results.

The task is solved by a protective device for the hand of a medical personnel when puncturing an umbilical cord of neonates, comprising: an umbilical cord channel for receiving the umbilical cord of the neonate, two wings arranged at the upper edge of the umbilical channel as hand protection, the wings each extending laterally away from the umbilical channel, and two handle strips, the handle strips being arranged on the two wings and one handle strip in each case extending from the lateral wings in the depth direction of the umbilical cord channel, the height of the respective handle strips corresponding at least to the depth of the umbilical cord channel, so that the umbilical cord channel is arranged between the two handle strips.

According to a variant of the device, the two wings extend along the entire length of the umbilical cord channel. This protects the holding hand of the medical personnel from puncture injuries, regardless of where the umbilical cord is punctured.

According to another variant, the two handle strips extend over the entire length of the umbilical cord channel. Such handle strips may enable particularly good handling of the protective device, in particular a secure grip in the hand of the medical personnel. The medical personnel may thus grip the protective device along its entire length, regardless of the size of the medical personnel's hand, since users can grip the protective device where it is comfortable for the medical personnel. Furthermore, the protective device may be placed stably on the two handle strips.

The two handle strips have the additional advantage that the device may be used equally by right-handed and left-handed persons.

In another variant, the handle strips each have at least one lateral indentation for a finger of the hand of the medical personnel. The indentations enable the protective device to be held even more securely in the hand of the medical personnel. In particular, the indentations are arranged in the proximal third of the protective device, for example for receiving the thumb and index finger of the hand of the medical personnel. Proximal in the sense of this disclosure is the end of the protective device facing the mother. Distal in the sense of this disclosure is the end of the protective device facing the medical personnel.

According to another variant, the umbilical cord channel is angled towards the proximal end in the depth direction of the umbilical cord channel. In this embodiment, the angulation is rounded and not angular. Due to the angulation, the umbilical cord is better fixed in the umbilical cord channel and the umbilical cord is not kinked at the ends of the protective device but is supported in the region of its usual course.

In some embodiments, the angle of the proximal end to the distal end of the umbilical cord channel is between 30 degrees and 60 degrees, or between 40 degrees and 50 degrees.

According to another variant, the lateral wings have the greatest lateral extension at the distal end and become continuously narrower towards the proximal end. At the distal end, in the intended use of the device, the palm of the medical personnel is arranged, while at the proximal end the fingertips are arranged. Since the fingertips are narrower overall than the palm and can also be held one on top of the other, the lateral wings can be less wide at the proximal end than at the distal end and still provide the same protection. The protective device may taper toward the proximal end, i.e., a protective device that narrows toward the proximal end and thus be less bulky and more ergonomic to use. Furthermore, the protective device can thus be better deposited on the groin of the mother.

In another variant, the umbilical cord channel has a constriction at the distal end and/or at the proximal end for fixing the umbilical cord. In particular, the constriction at the distal end and/or proximal end may be V-shaped. Such a constriction helps to fix the umbilical cord in the umbilical cord channel by its own weight without pinching off the umbilical cord or reducing the blood flow to the umbilical cord.

According to another variant, the inner side of the umbilical cord channel is designed to be softer than a puncture needle, so that the puncture needle can be fixed in the inner side of the umbilical cord channel when piercing through the umbilical cord. In particular, the inner side of the umbilical cord channel may be designed to be flexible for this purpose. This has the advantage that after puncture and sampling, the puncture needle can be pierced through the umbilical cord and fixed in the inside of the umbilical cord channel. The puncture needle can remain there until the umbilical cord has been separated and set aside. Puncture injuries after specimen collection are thus also reliably prevented. For example, the inside of the umbilical cord channel has an extra coating, or the umbilical cord channel may be made of a softer material, in particular plastic, but may have sufficient wall thickness to prevent puncture with the puncture needle.

In addition, several blood samples are usually taken from the umbilical cord. For example, the umbilical artery is punctured first to determine the arterial pH. Subsequently, the umbilical vein may be punctured to determine venous pH. In addition, blood for an EDTA tube for blood grouping or serum for serologies can still be collected from the umbilical cord. The puncture needle used for this may be fixed in the softer inner side of the umbilical cord channel in various embodiments.

The disclosed protective device for the hand of a medical personnel when puncturing an umbilical cord of neonates may have, for example, a length between 10 cm and 20 cm, in particular about 15 cm. The umbilical cord channel of the protective device may thereby be curved, U-shaped, polygonal or the like. In various embodiments, the umbilical cord channel may have an upper width of 15 mm to 25 mm, or about 20 mm. The lateral wings have a width of 1.0 cm to 5.0 cm, or about 2.5 cm. In some embodiments, the lateral wings have the greatest lateral extent at the distal end and become continuously narrower toward the proximal end. For example, the lateral wings may have a width of 2.5 cm to 5.0 cm at the distal end and taper to 1.0 cm to 2.5 cm toward the proximal end.

BRIEF DESCRIPTION OF THE DRAWINGS

The invention is explained in more detail below with reference to examples of embodiments shown in the figures.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" (or "comprises") means "including (or includes), but not limited to." When used in this document, the term "exemplary" is intended to mean "by way of example" and is not intended to indicate that a particular exemplary item is preferred or required.

In this document, when terms such as "first" and "second" are used to modify a noun, such use is simply intended to distinguish one item from another, and is not intended to require a sequential order unless specifically stated. The term "approximately," when used in connection with a numeric value, is intended to include values that are close to, but not exactly, the number. For example, in some embodiments, the term "approximately" may include values that are within +/−10 percent of the value.

Figure 1:
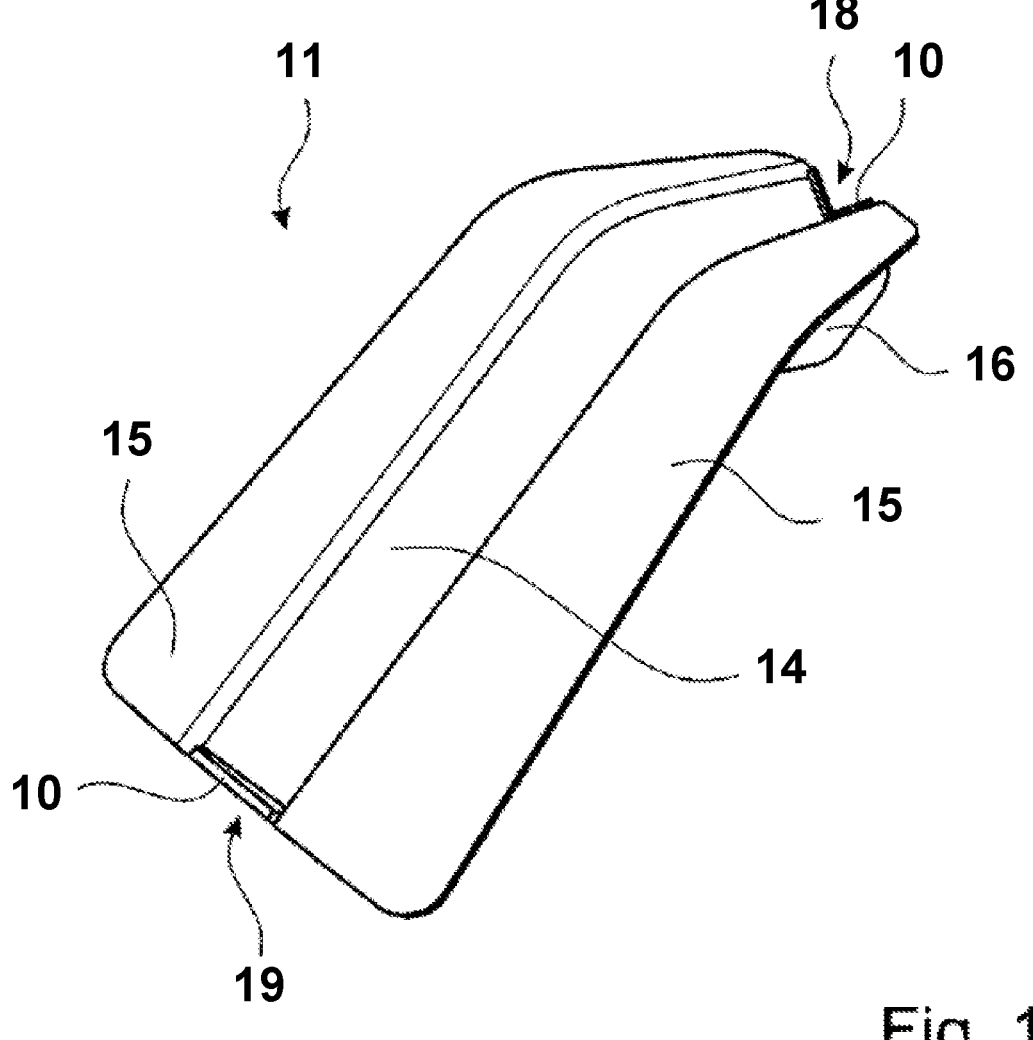
FIG. 1 shows a top perspective view of a protective device for the hand of a medical personnel when puncturing an umbilical cord of neonates according to the invention.

FIG. 1 shows a perspective top view of a protective device 11 for the hand 12 of a medical personnel when puncturing an umbilical cord 13 of neonates. The protective device 11 comprises an umbilical cord channel 14 for receiving the umbilical cord of the neonate and two wings 15 arranged at the upper edge of the umbilical cord channel 14 as hand protection. The wings 15 extend laterally away from the umbilical cord channel 14 in the use position of the protective device 11.

The protective device 11 further comprises two handle strips 16 arranged on the two wings 15. One handle strip 16 extends from each of the lateral wings 15 in the depth direction of the umbilical cord channel 14. The height of the two handle strips 16 corresponds at least to the depth of the umbilical cord channel 14. The umbilical cord channel 14 is thus arranged between the two handle strips 16.

The protective device 11 may have, for example, a length between 10 cm and 20 cm, such as approximately 15 cm. The umbilical cord channel 14 of the protective device 11 is, for example, curved, U-shaped or polygonal and may have an upper width of 15 mm to 25 mm, such as approximately 20 mm. According to the embodiment example shown in FIG. 1, the umbilical cord channel 14 has a constriction 10 at the distal end 19 and at the proximal end 18, respectively, for fixing the umbilical cord 13. For example, this constriction 10 is V-shaped. The constriction 10 provides better fixation of the umbilical cord 13 in the umbilical cord channel 14, but the constriction 10 is designed in such a way that the umbilical cord 13 and in particular the blood flow through the umbilical cord 3 is not pinched off.

As can be seen from FIG. 1, the two wings 15 extend along the entire length of the umbilical cord channel 14. The two wings 51 have a greater lateral extent at the distal end 19 of the protective device 11 than at the proximal end 18. In particular, the lateral wings 15 become continuously narrower toward the proximal end 18. For example, the two wings 15 have a width of 2.5 cm to 5.0 cm at the distal end 19 and a width of 1.0 cm to 2.5 cm at the proximal end. According to a variant, the inner side of the umbilical cord channel 14 may be designed to be softer than a puncture needle 11, so that the puncture needle 11 can be fixed in the inner side of the umbilical cord channel 14 when piercing through the umbilical cord 3 and at the same time the leakage of umbilical cord blood can be reduced. In particular, the inner side of the umbilical cord channel 14 may be designed to be flexible for this purpose. This has the advantage that after puncture and sampling, the puncture needle 11 can be pierced through the umbilical cord 13 and fixed in the inner side of the umbilical cord channel 14. The puncture needle 11 can remain there until the umbilical cord 13 has been separated and set aside. Puncture injuries after sampling are thus also reliably prevented. For example, the inside of the umbilical cord channel 14 has an extra coating or the umbilical cord channel 14 is made of a softer material, in particular plastic, but has sufficient wall thickness to prevent puncturing with the puncture needle 11.

Figure 2:
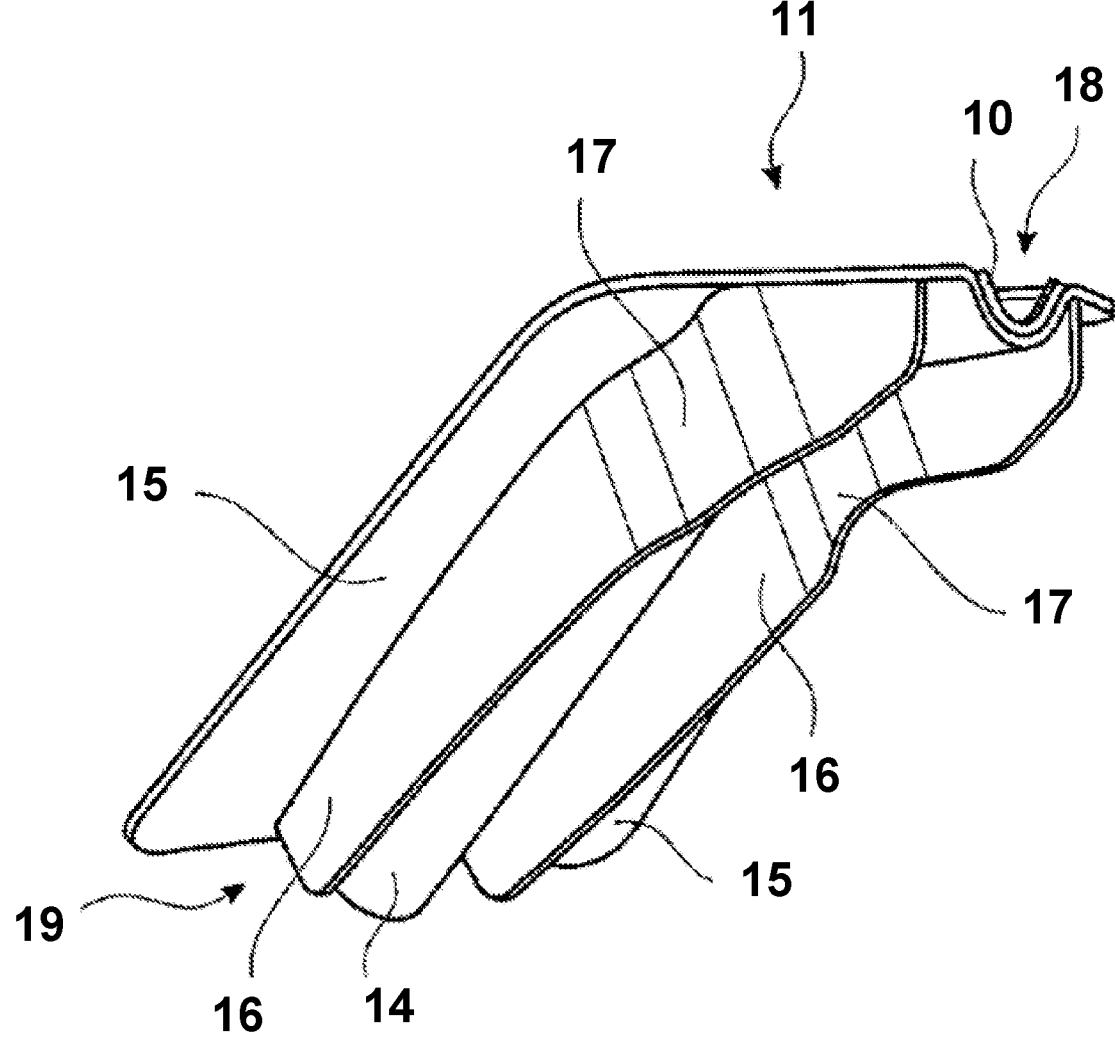
FIG. 2 shows a perspective view from below of the protective device of FIG. 1.

FIG. 2 shows a perspective view from below of the protective device 11 from FIG. 1. As can be seen in particular from FIG. 2, the two handle strips 16 extend almost over the entire length of the umbilical cord channel 14 or of the protective device 1. The two handle strips 6 each have an indentation 17, each for a finger of the hand 12 of the medical personnel, in particular the thumb and index finger of the hand 12. The indentations 17 are arranged approximately in the proximal third of the protective device 11.

Figure 3:
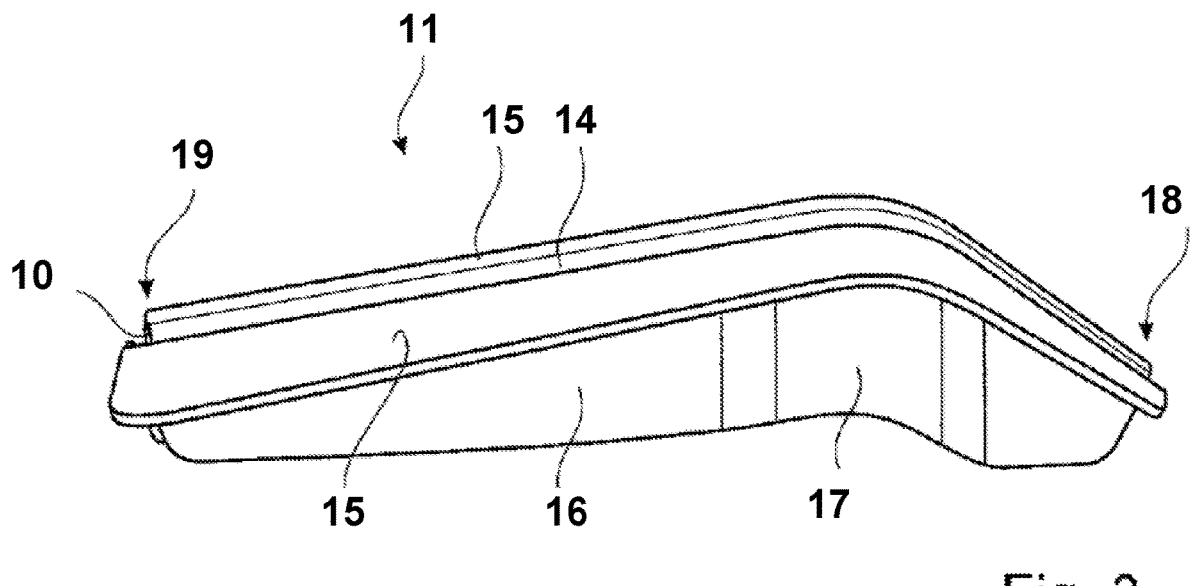
FIG. 3 shows a side view of the protective device of FIGS. 1 and 2.

FIG. 3 shows a side view of the protective device 11 from FIGS. 1 and 2. It can be seen particularly well from FIG. 3 that the umbilical cord channel 14 is angled towards the proximal end 18 in the depth direction of the umbilical cord channel 14, i.e. downwards in the position of use of the protective device 11. According to the invention, the angle of the proximal end 18 to the distal end 19 of the umbilical cord channel 14 is between 30 degrees and 60 degrees, or between 40 degrees and 50 degrees.

It can also be seen from FIG. 3 that the indentations 17 on the handle strips 16 are arranged approximately in the area of the bend and that the protective device 11 can be laid down in a stable manner on the two handle strips 16. Since the two handle strips 16 are arranged on opposite sides of the umbilical cord channel 14, the umbilical cord 13 can also be punctured in the laid-down state, in particular without the protective device 11 tipping away laterally.

Figure 4:
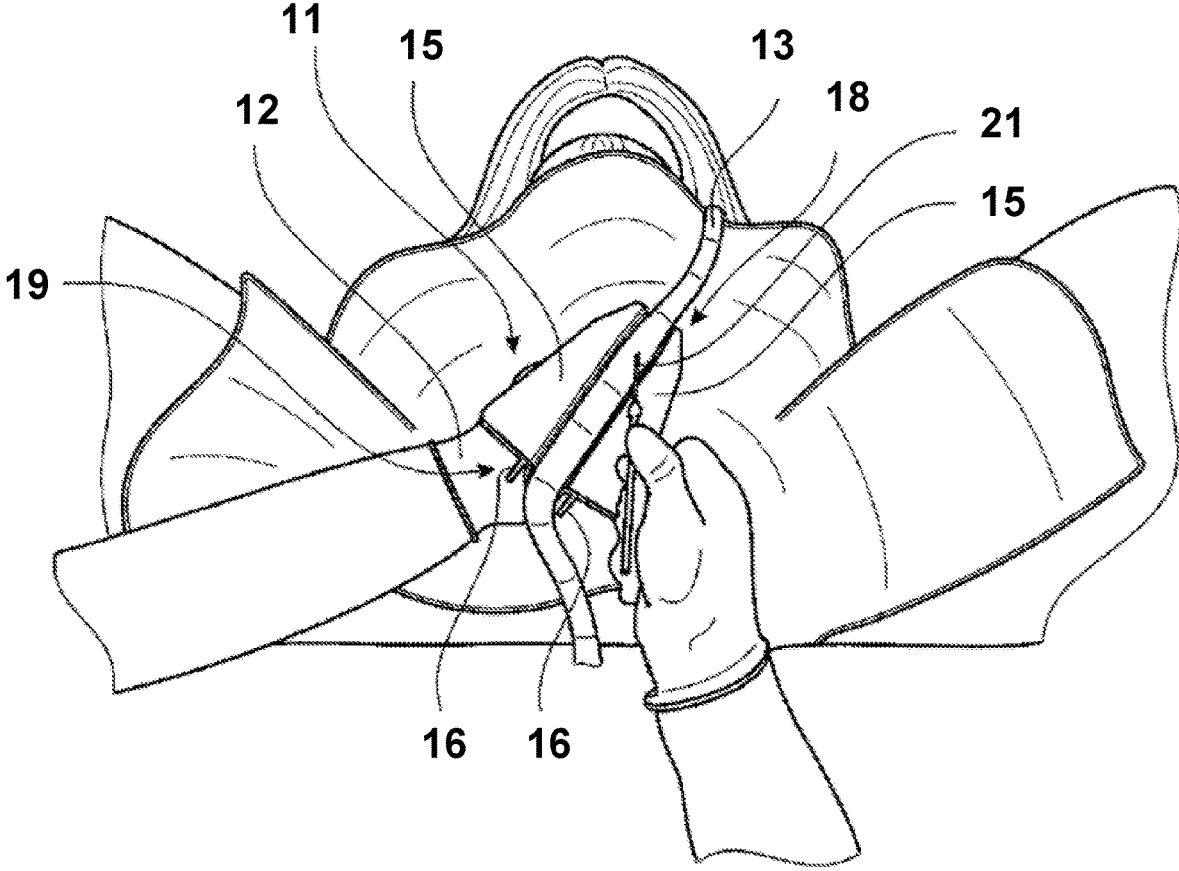
FIG. 4 shows a protective device for the hand of a medical personnel during the puncture of an umbilical cord of a neonate.

FIG. 4 shows a protective device 11 for the hand 12 of a medical personnel during the puncture of an umbilical cord 13 of a neonate. The medical personnel can hold the protective device 11 in one hand 12 by means of the handle strips 16 arranged below the two wings 15 in the position of use. The umbilical cord 13 of the neonate is placed in the umbilical cord channel 14 and can be punctured with the other hand of the medical personnel by means of a puncture needle 21. The umbilical cord channel 14 protects the hand 12 of the medical personnel from puncture injuries caused by piercing the umbilical cord 13, and the lateral wings 15 protect the hand 12 of the medical personnel from puncture injuries caused by slipping or the like from the umbilical cord channel 14, for example, due to unforeseen movements of the mother and/or the neonate. Since the hand 12 for holding the protective device 11 is positioned completely below the wings 15, the umbilical cord 13 placed in the umbilical cord channel 14 can be punctured anywhere along the complete length of the umbilical cord channel 14 without the risk of puncture injuries.

The protective device can be held in one hand by the medical personnel by means of the two handle strips. The umbilical cord channel, which is arranged between the two handle strips, extends through the palm of the medical personnel's hand, which corresponds to a particularly ergonomic position for puncturing the umbilical cord. The umbilical cord channel prevents puncture injuries caused by unintentional piercing of the umbilical cord. The wings arranged on the upper edge of the umbilical cord channel, protect the hand of the medical personnel from puncture injuries caused by slipping of the needle or other unwanted movements, for example caused by movements of the mother or the neonate. The holding hand of the medical personnel is thus located below the umbilical cord channel and is protected from above by the lateral wings. Due to this arrangement, the umbilical cord can be punctured at any point of the umbilical cord channel, especially at a point where a corresponding vessel of the umbilical cord is clearly visible for blood sampling. In contrast, for example, in the prior art according to EP 2 913 004 A1, the umbilical cord can only be punctured in the puncture area of the umbilical cord channel, which is further located in close proximity to the fixing section where the medical personnel fix the umbilical cord on the upper side of the umbilical cord channel with a finger.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A protective device for a hand of a medical personnel when puncturing an umbilical cord of a neonate, comprising:

an umbilical cord channel for receiving the umbilical cord of the neonate;

two wings arranged at an upper edge of the umbilical cord channel and configured to act as hand protection, the wings each extending laterally away from the umbilical cord channel; and two handle strips each having a top end and a bottom end defining a height of the handle strip, the handle strips being connected to the two wings via the top end only and each handle strip case extending from the lateral wings in a depth direction of the umbilical cord channel, the height of the respective handle strips corresponding at least to the depth of the umbilical cord channel, the two handle strips formed separately from the umbilical cord channel so that the umbilical cord channel is arranged between the two handle strips, wherein the two wings are configured to extend over a hand of the medical personnel when the device is gripped by the two handle strips.

2. The protective device according to claim 1, wherein the two wings extend over the entire length of the umbilical channel.

3. The protective device according to claim 1, wherein the two handle strips extend over the entire length of the umbilical channel.

4. The protective device according to claim 1, wherein the handle strips each have at least one lateral indentation in the bottom end thereof configured for a finger of the hand of the medical personnel.

5. The protective device according to claim 1, wherein the umbilical cord channel is angled towards the proximal end in a depth direction of the umbilical cord channel.

6. The protective device according to claim 5, wherein the angle of the proximal end of the umbilical cord channel to a distal end of the umbilical cord channel is between 30 degrees and 60 degrees.

7. The protective device according to claim 6, wherein the angle of the proximal end of the umbilical cord channel to the distal end of the umbilical cord channel is between 40 degrees and 50 degrees.

8. The protective device according to claim 1, wherein the lateral wings have a greatest lateral extension at a distal end of the umbilical cord channel and becomes continuously narrower towards a proximal end of the umbilical cord channel.

9. The protective device according to claim 1, wherein the umbilical cord channel has a constriction at a distal end and/or at a proximal end for fixing the umbilical cord.

10. The protective device according to claim 9, wherein the constriction at the distal end and/or the proximal end is V-shaped.

11. The protective device according to claim 1, wherein an inner side of the umbilical cord channel is configured to be formed softer than a puncture needle, so that the puncture needle can be fixed in the inner side of the umbilical cord channel when piercing through the umbilical cord.

* * * * *